US009839434B2

(12) United States Patent
Romano et al.

(10) Patent No.: US 9,839,434 B2
(45) Date of Patent: Dec. 12, 2017

(54) PATIENT-SPECIFIC MILL GUIDE

(75) Inventors: Anthony P. Romano, Columbia City, IN (US); Justin J. May, Leesburg, IN (US)

(73) Assignee: ZIMMER, INC., Warsaw, IN (US)

(*) Notice: Subject to any disclaimer, the term of this patent is extended or adjusted under 35 U.S.C. 154(b) by 5 days.

(21) Appl. No.: 12/907,292

(22) Filed: Oct. 19, 2010

(65) Prior Publication Data

US 2011/0106093 A1 May 5, 2011

Related U.S. Application Data

(60) Provisional application No. 61/256,067, filed on Oct. 29, 2009.

(51) Int. Cl.
*A61B 17/56* (2006.01)
*A61B 17/15* (2006.01)
(Continued)

(52) U.S. Cl.
CPC ........ *A61B 17/155* (2013.01); *A61B 17/1675* (2013.01); *A61B 17/1764* (2013.01);
(Continued)

(58) Field of Classification Search
CPC . A61B 17/17; A61B 17/1703; A61B 17/1717; A61B 17/1735; A61B 17/1739;
(Continued)

(56) References Cited

U.S. PATENT DOCUMENTS 4,841,975 A 6/1989 Woolson
5,098,383 A 3/1992 Hemmy et al.
(Continued)

FOREIGN PATENT DOCUMENTS

AU 2004293091 A1 6/2005
AU 2004293104 A1 6/2005
(Continued)

OTHER PUBLICATIONS

"Computer-Integrated Orthopaedic Surgery: Connection of Planning and Execution in Surgical Intervention", Klaus Radermacher et al., pp. 451-463 of the Book Computer-Integrated Surgery—Technology and Clinical Applications edited by Russell H. Taylor et al., The Mit Press, Cambridge, Massachusetts/London, England, British Library Document Supply Centre Nov. 2, 1995.
(Continued)

*Primary Examiner* — Kevin T Truong
*Assistant Examiner* — Tracy Kamikawa
(74) *Attorney, Agent, or Firm* — Norton Rose Fulbright Canada LLP

(57) ABSTRACT

An orthopedic guide for preparing a particular patient's bone to receive a prosthesis using a milling tool with a rotating burr comprises a platform having a top surface and a bottom surface adapted to face the patient's bone. The platform defines an elongate milling track that extends through the platform from the top surface to the bottom surface of the platform, the milling track being sized and shaped so as to be adapted to guide the milling tool across the patient's bone with the burr of the milling tool rotating beneath the bottom surface of the platform to be adapted to remove a first bone portion from the patient's bone. A plurality of legs are coupled to the platform and each comprise a referencing end that is contour-matching fabricated as a function of the patient's bone data to be adapted to abut the patient's bone, the referencing ends of the plurality of legs adapted to cooperate to locate the orthopedic guide at a single predetermined location of the patient's bone.

20 Claims, 16 Drawing Sheets

(51) Int. Cl.
  *A61B 17/16* (2006.01)
  *A61B 17/17* (2006.01)
  *A61F 2/30* (2006.01)
  *A61F 2/38* (2006.01)
  *A61B 90/00* (2016.01)

(52) U.S. Cl.
  CPC . *A61B 2017/1602* (2013.01); *A61B 2017/568* (2013.01); *A61B 2090/034* (2016.02); *A61F 2/30942* (2013.01); *A61F 2/3859* (2013.01); *A61F 2/3877* (2013.01); *A61F 2002/30971* (2013.01); *A61F 2002/3895* (2013.01); *A61F 2240/001* (2013.01); *A61F 2240/002* (2013.01)

(58) Field of Classification Search
  CPC ... A61B 17/1764; A61B 17/15; A61B 17/154; A61B 17/155
  USPC ......... 606/80, 82, 84, 85, 86 R–89, 96, 102, 606/104
  See application file for complete search history.

(56) References Cited

U.S. PATENT DOCUMENTS

| | | | |
|---|---|---|---|
| 5,474,559 A * | 12/1995 | Bertin et al. | 606/89 |
| 5,490,854 A | 2/1996 | Fisher et al. | |
| 5,743,915 A * | 4/1998 | Bertin et al. | 606/88 |
| 5,768,134 A | 6/1998 | Swaelens et al. | |
| 5,853,415 A | 12/1998 | Bertin et al. | |
| 5,871,018 A | 2/1999 | Delp et al. | |
| 5,916,219 A | 6/1999 | Matsuno et al. | |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 | 5/2009 | Burdulis | |
| 7,618,451 B2 | 11/2009 | Berez et al. | |
| 7,634,119 B2 | 12/2009 | Tsougarakis et al. | |
| 7,717,956 B2 | 5/2010 | Lang | |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,545,569 B2 | 10/2013 | Fitz et al. | |
| 8,551,099 B2 | 10/2013 | Lang | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,585,708 B2 | 11/2013 | Fitz et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 2003/0055502 A1 | 3/2003 | Lang et al. | |
| 2003/0216669 A1 | 11/2003 | Lang et al. | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0204644 A1 | 10/2004 | Tsougarakis et al. | |
| 2004/0204760 A1 | 10/2004 | Fitz et al. | |
| 2004/0236424 A1 | 11/2004 | Berez et al. | |
| 2005/0148843 A1 | 7/2005 | Roose | |
| 2005/0234461 A1 | 10/2005 | Burdulis et al. | |
| 2005/0267584 A1 | 12/2005 | Burdulis et al. | |
| 2006/0111722 A1 | 5/2006 | Bouadi | |
| 2006/0122617 A1 * | 6/2006 | Lavallee et al. | 606/87 |
| 2006/0276796 A1 * | 12/2006 | Creger | A61B 17/1767 606/79 |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0173815 A1 | 7/2007 | Murase | |
| 2007/0198022 A1 | 8/2007 | Lang et al. | |
| 2007/0226986 A1 | 10/2007 | Park et al. | |
| 2007/0233141 A1 | 10/2007 | Park et al. | |
| 2007/0233269 A1 | 10/2007 | Steines et al. | |
| 2007/0250169 A1 | 10/2007 | Lang | |
| 2007/0288030 A1 | 12/2007 | Metzger et al. | |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0188942 A1 | 8/2008 | Brown et al. | |
| 2008/0195216 A1 | 8/2008 | Philipp | |
| 2008/0215059 A1 | 9/2008 | Carignan et al. | |
| 2008/0234683 A1 | 9/2008 | May | |
| 2008/0243127 A1 | 10/2008 | Lang et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1 | 11/2008 | Kunz et al. | |
| 2008/0312659 A1 | 12/2008 | Metzger et al. | |
| 2008/0319491 A1 | 12/2008 | Schoenefeld | |
| 2009/0024131 A1 | 1/2009 | Metzgu et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 * | 4/2009 | Aram et al. | 606/87 |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0110498 A1 | 4/2009 | Park et al. | |
| 2009/0131941 A1 | 5/2009 | Park et al. | |
| 2009/0131942 A1 | 5/2009 | Aker et al. | |
| 2009/0138020 A1 | 5/2009 | Park et al. | |
| 2009/0157083 A1 | 6/2009 | Park et al. | |
| 2009/0163922 A1 | 6/2009 | Meridew et al. | |

(56) References Cited

U.S. PATENT DOCUMENTS

| | | |
|---|---|---|
| 2009/0220134 A1 | 9/2009 | Cahill et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0254093 A1 | 10/2009 | White et al. |
| 2009/0270868 A1 | 10/2009 | Park et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0076441 A1 | 3/2010 | May et al. |
| 2010/0082034 A1 | 4/2010 | Remia |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1* | 8/2010 | Carroll ............ A61B 17/155 606/86 R |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |

(56) References Cited

U.S. PATENT DOCUMENTS

| | | |
|---|---|---|
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0086780 A1 | 3/2014 | Miller et al. |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 | 3/2011 |
| DE | 60239674 | 5/2011 |
| DE | 602004032166 | 5/2011 |
| DE | 602005027391 | 5/2011 |
| EP | 1374782 A2 | 1/2004 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |

(56) References Cited

FOREIGN PATENT DOCUMENTS

| | | | |
|---|---|---|---|
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | WO93/25157 A1 | 12/1993 |
| WO | WO02/096271 A2 | 12/2002 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | WO2006/127283 A2 | 11/2006 |
| WO | WO2006/135462 A2 | 12/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | WO2008/117028 A1 | 10/2008 |
| WO | 2008101090 A3 | 11/2008 |
| WO | 2008157412 A2 | 12/2008 |
| WO | WO2009/001083 A1 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | WO2009/111512 A2 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

"Image Guided Orthopedic Surgery Using Individual Templates", Experimental Results and Aspects of the Development of a Demonstrator for Pelvis Surgery—K. Radermacher et al., Image Guided Orthopedic Surgery, EC-Project HC1026HC, Health Care Sector, Telematics Applications Program, pp. 606-615, date unknown.

"Computer Assisted Matching of Planning and Execution in Orthopedic Surgery", K. Radermacher et al., 0-7803-1377, Jan. 1993, IEEE, pp. 946-947

"Image-Based Planning and Validation of C1-C2 Transarticular Screw Fixation Using Personalized Drill Guides", Johan Van Cleynenbreugel et al., Received Oct. 15, 1999, Accepted Dec. 16, 2001, Computer Aided Surgery 7:41-48 (2002).

International Search Report and Written Opinion dated Mar. 22, 2011 in related International Application No. PCT/US2010/053134.

Hofmann et al, "Natural-Knee II System", Intermedics Orthopedics, Austin, TX, 1995.

* cited by examiner

PATIENT-SPECIFIC MILL GUIDE

CROSS REFERENCE TO RELATED APPLICATION

This application claims priority from U.S. Provisional Patent Application Ser. No. 61/256,067, entitled "PATIENT-SPECIFIC MILL GUIDE," filed Oct. 29, 2009, the disclosure of which is hereby expressly incorporated by reference herein in its entirety.

BACKGROUND

1. Field of the Invention

The present invention relates to surgical systems and orthopedic prostheses. More particularly, the present invention relates to patient-specific surgical systems and orthopedic prostheses.

2. Description of the Related Art

A joint arthroplasty procedure may be performed to repair a damaged bone of a joint. In operation, a surgeon may use a milling system to prepare the damaged bone for receiving an orthopedic prosthesis. For example, during a total or partial knee arthroplasty procedure, the surgeon may mill the distal femur to provide an attachment surface for receiving a distal femoral prosthesis. The distal femoral prosthesis includes a bone-engaging surface configured to rest against the prepared attachment surface of the distal femur and an articulating surface that may be designed to articulate with the proximal tibia or the patella, for example. The distal femoral prosthesis may be a unicompartmental implant, a bicompartmental implant, or a total femoral implant, for example.

SUMMARY

The present invention provides a patient-specific surgical system, such as a patient-specific milling guide, for preparing a bone to receive an orthopedic prosthesis.

According to an embodiment of the present invention, an orthopedic guide is provided for preparing a particular patient's bone to receive a prosthesis using a milling tool with a rotating burr. The orthopedic guide includes a platform and a plurality of legs coupled to the platform. The platform has a top surface and a bottom surface that faces the patient's bone, the platform defining an elongate milling track that extends through the platform from the top surface to the bottom surface of the platform, the milling track being sized and shaped to guide the milling tool across the patient's bone with the burr of the milling tool rotating beneath the bottom surface of the platform to remove a first bone portion from the patient's bone. Each of the plurality of legs includes a referencing end that is contoured to abut the patient's bone, the referencing ends of the plurality of legs cooperating to locate the orthopedic guide at a predetermined location of the patient's bone.

According to another embodiment of the present invention, a method is provided for preparing a particular patient's bone to receive a prosthesis having an articulating surface and a bone-engaging surface. The method includes the steps of: providing a digital model of the bone; identifying a portion of the bone to be removed to receive the prosthesis; providing a patient-specific guide; using the patient-specific guide to remove the identified portion of the bone, thereby forming a prepared surface of the bone; and inlaying the prosthesis into the bone by positioning the bone-engaging surface of the prosthesis against the prepared surface of the bone, the articulating surface of the prosthesis transitioning smoothly into a remaining surface of the bone located adjacent to the prepared surface of the bone.

According to yet another embodiment of the present invention, a method is provided for preparing a particular patient's bone to receive a prosthesis. The method includes the steps of: providing a digital model of the bone; providing a digital model of the prosthesis, the digital model of the prosthesis having a bone-contacting surface with a predetermined shape; identifying a portion of the bone to be removed to receive the bone-contacting surface of the prosthesis; providing a patient-specific guide to remove the identified portion of the bone; and manufacturing the prosthesis to fill at least the removed portion of the bone.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 10:
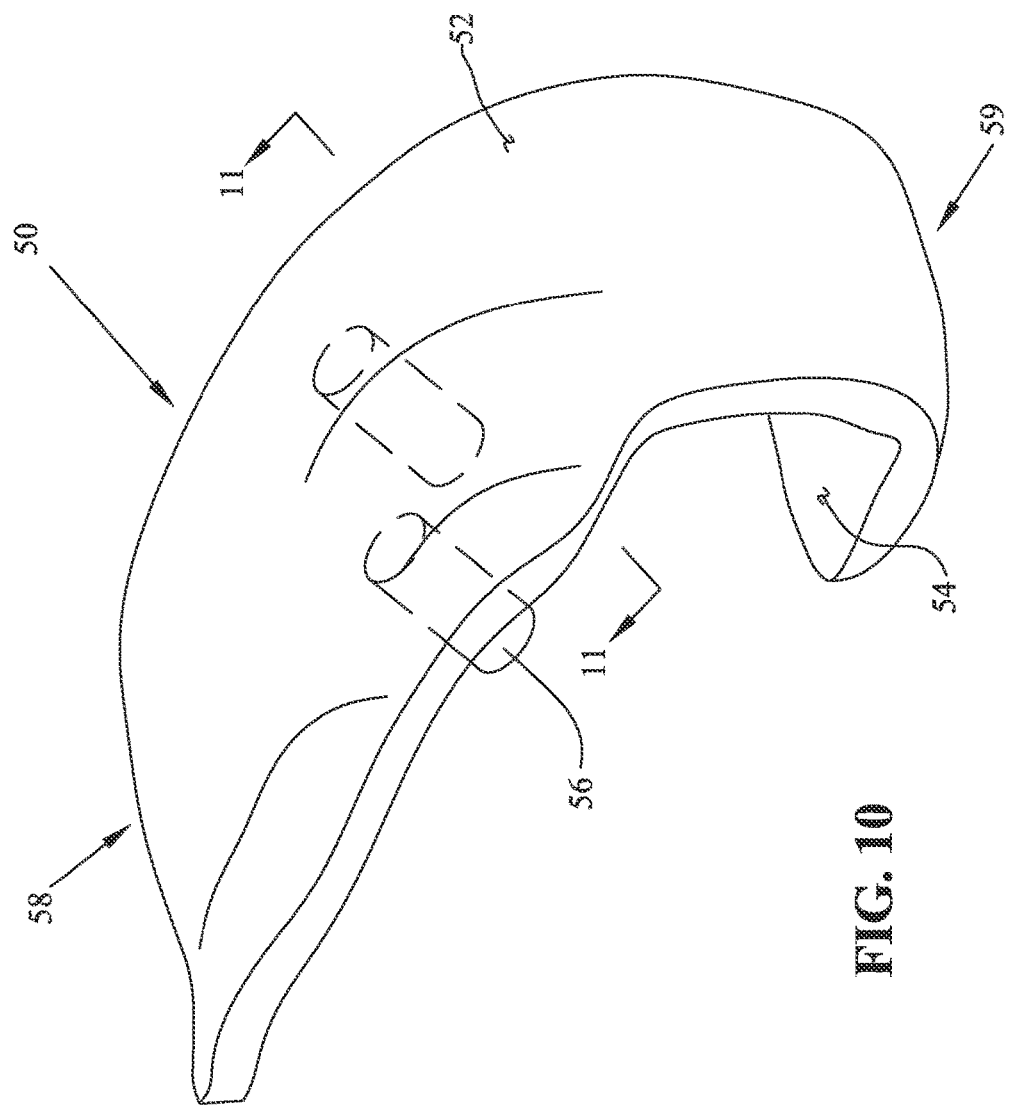
FIG. 10 is a lateral perspective view of an exemplary distal femoral prosthesis of the present invention.

Orthopedic system 10 is provided for preparing femur 100 to receive a distal femoral prosthesis 50 (FIG. 10). An exemplary orthopedic system 10 includes a patient-specific guide 12 (FIGS. 1-6), a milling tool 14 (FIG. 7A), and optionally a cutting tool 16 (FIG. 7B). Although orthopedic system 10 is described and depicted herein as being used to prepare femur 100, orthopedic system 10 may be used to prepare other anatomical structures, such as the tibia, radius, ulna, and other bones, to receive corresponding orthopedic prostheses.

Figure 1:
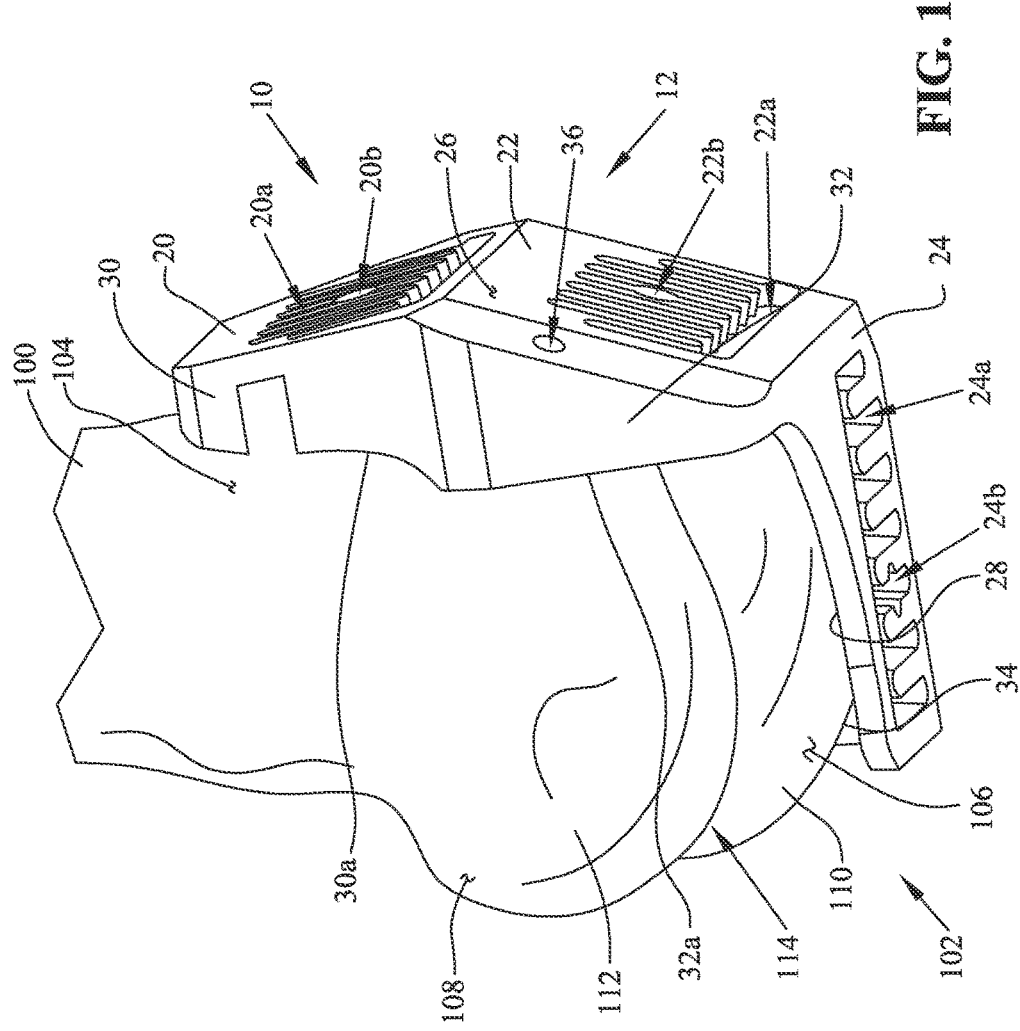
FIG. 1 is a lateral perspective view of an exemplary patient-specific guide of the present invention positioned against a distal femur.
Figure 2:
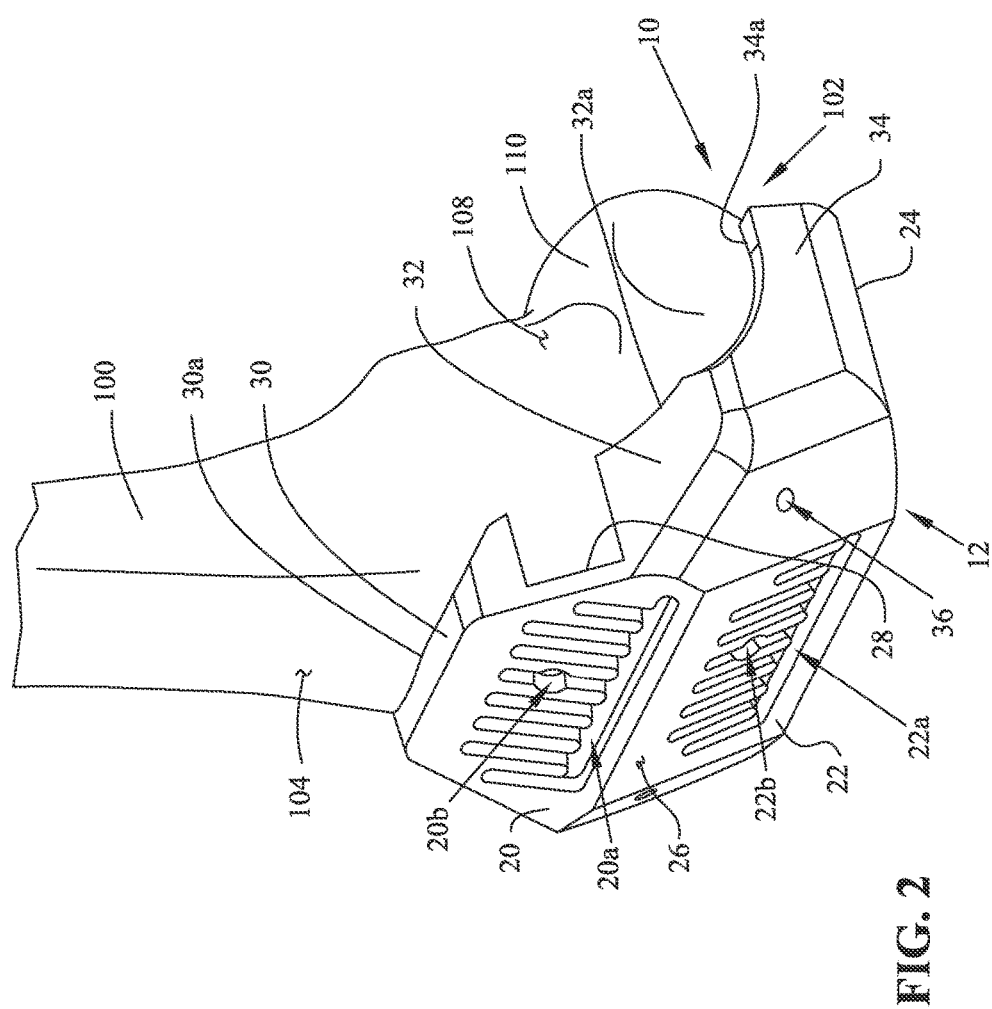
FIG. 2 is a medial perspective view of the patient-specific guide of FIG. 1 positioned against the distal femur.

As shown in FIG. 1, distal end 102 of femur 100 includes anterior surface 104, distal surface 106, and posterior surface 108. Also, distal end 102 of femur 100 includes medial condyle 110, lateral condyle 112, and intercondylar notch 114 located between medial condyle 110 and lateral condyle 112. During flexion and extension of the knee, medial condyle 110 and lateral condyle 112 of femur 100 articulate against the proximal end of a tibia (not shown), and a patella (not shown) glides across anterior surface 104 of femur 100.

Referring to FIGS. 1-6, an exemplary guide 12 of orthopedic system 10 includes anterior platform 20, intermediate platform 22 that extends obtusely from anterior platform 20, and distal platform 24 that extends obtusely from intermediate platform 22. Distal platform 24 may be transverse or substantially perpendicular to anterior platform 20. Guide 12 also includes top surface 26 and an opposing bottom surface 28 that span platforms 20, 22, 24.

Figure 3:
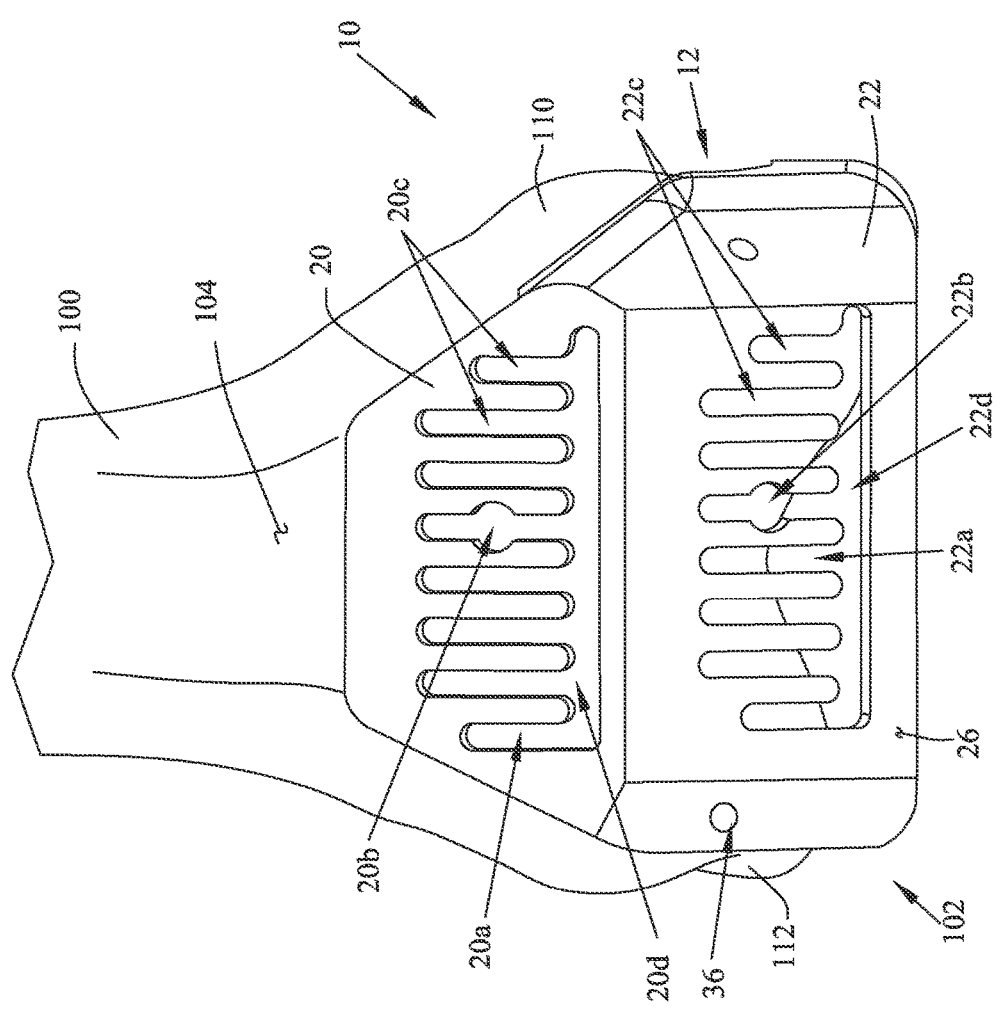
FIG. 3 is an anterior elevational view of the patient-specific guide of FIG. 1 positioned against the distal femur.
Figure 4:
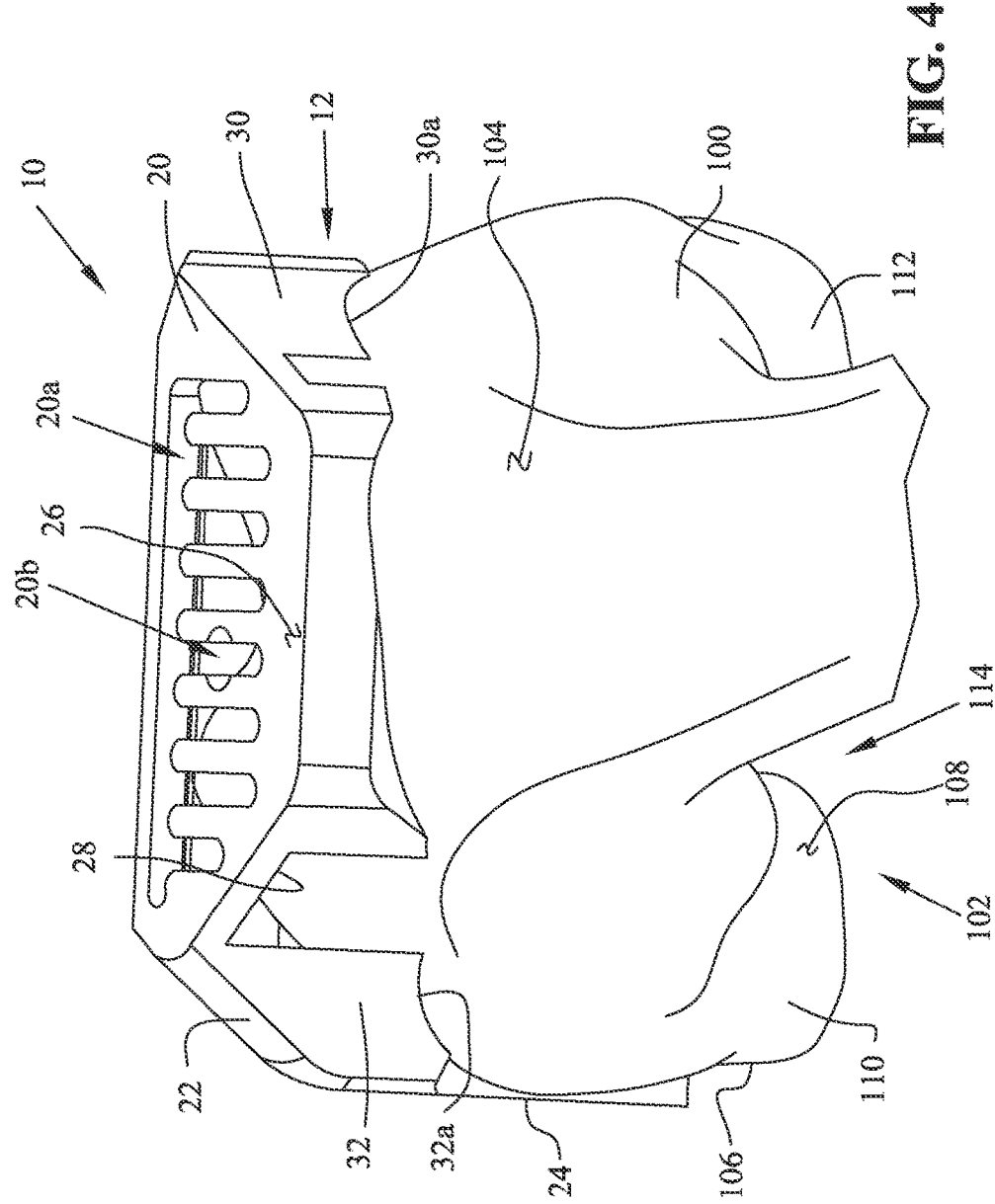
FIG. 4 is a proximal plan view of the patient-specific guide of FIG. 1 positioned against the distal femur.
Figure 5:
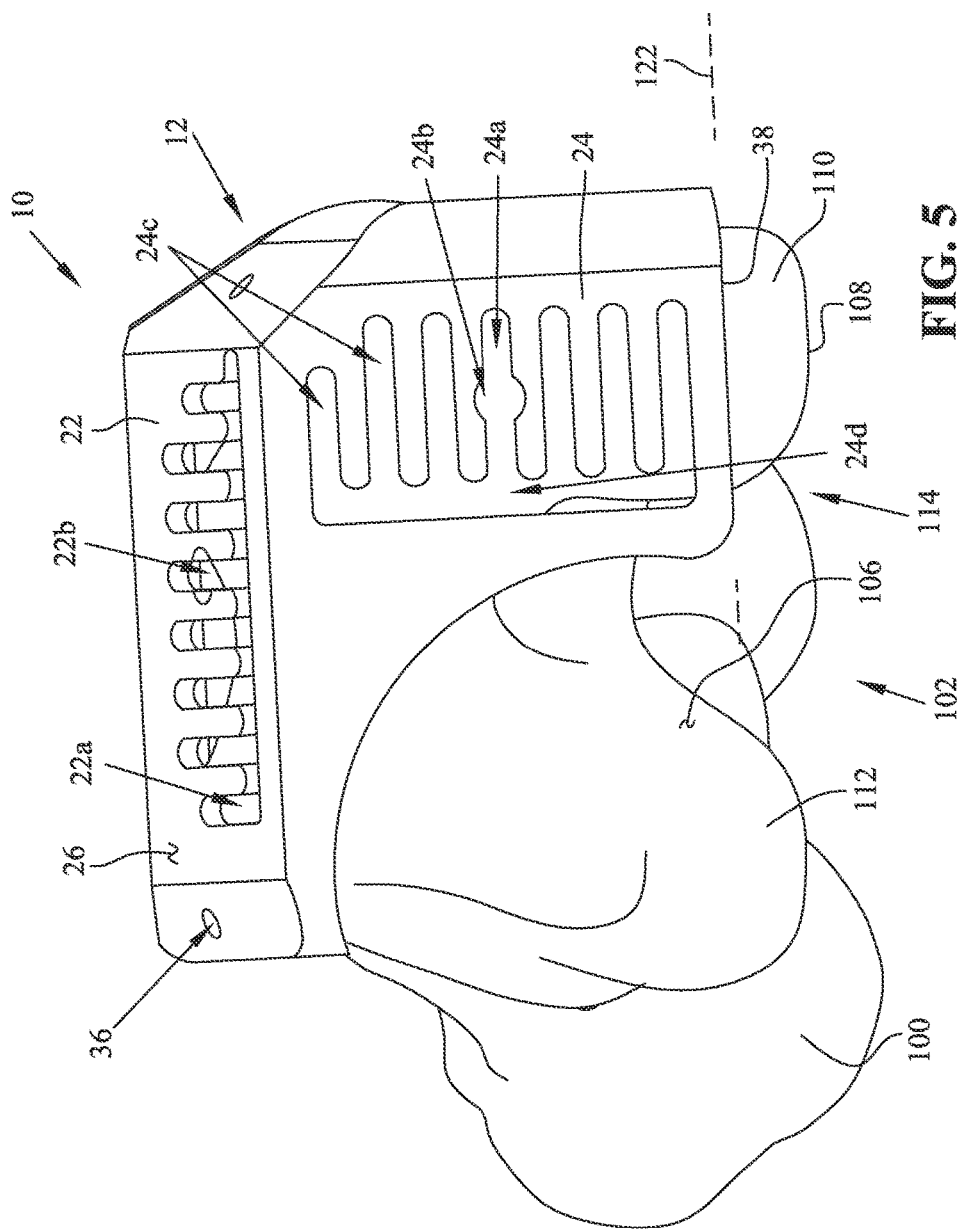
FIG. 5 is a distal plan view of the patient-specific guide of FIG. 1 positioned against the distal femur.
Figure 6:
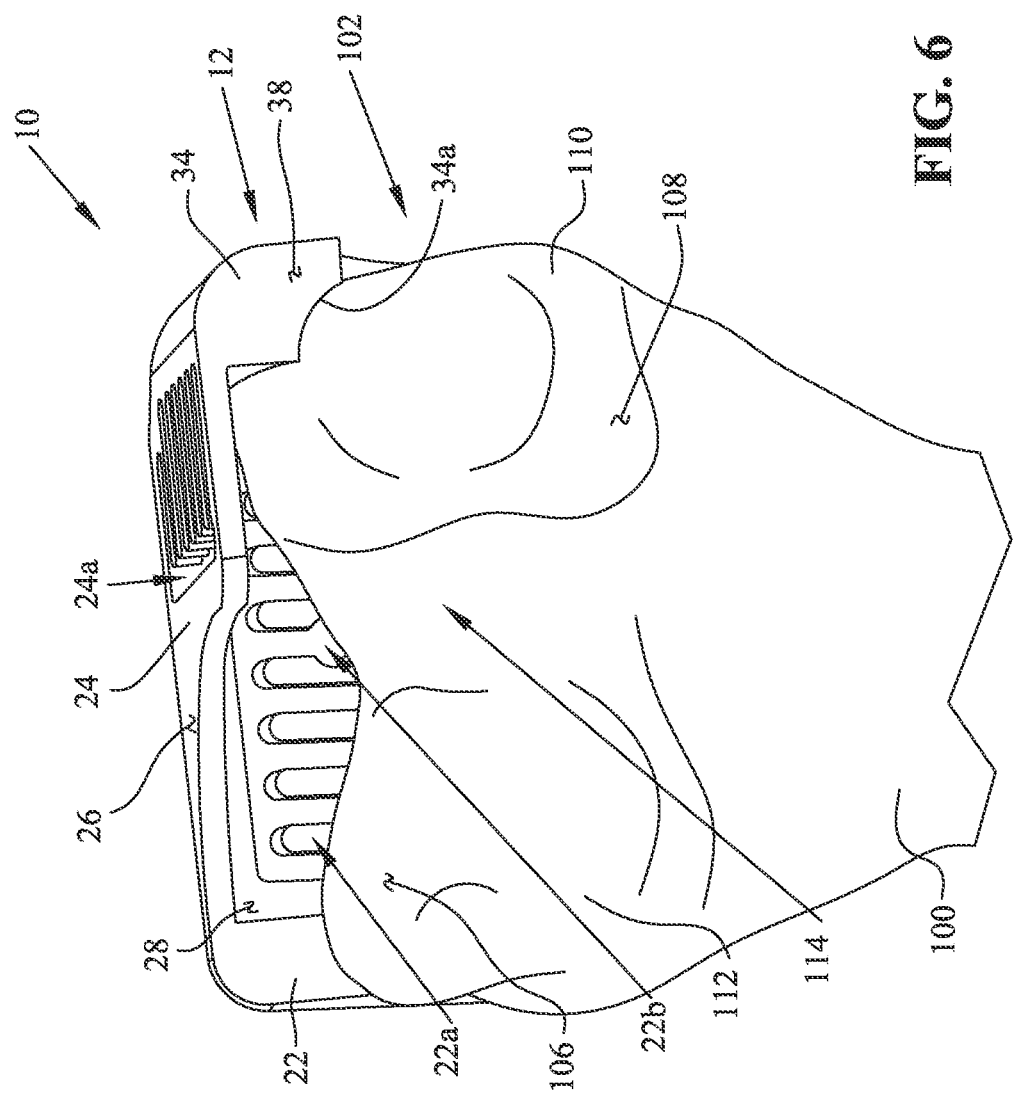
FIG. 6 is a posterior perspective of the patient-specific guide of FIG. 1 positioned against the distal femur.

Guide 12 further includes milling tracks 20a, 22a, 24a, that are defined by platforms 20, 22, 24, respectively, for guiding milling tool 14 (FIG. 7A) across distal end 102 of femur 100. Each milling track 20a, 22a, 24a, of guide 12 extends entirely through its respective platform 20, 22, 24, from top surface 26 to bottom surface 28. The number, size, and arrangement of milling tracks 20a, 22a, 24a, may vary depending on the particular instrument being used and the desired resection of femur 100, for example. Each milling track 20a, 22a, 24a, of guide 12 includes an opening 20b, 22b, 24b, that is larger in size than the respective milling track 20a, 22a, 24a, to receive milling tool 14 therein, as described further below. Aside from openings 20b, 22b, 24b, milling tracks 20a, 22a, 24a, are narrow in width to capture milling tool 14 therein. As shown in FIGS. 3 and 5, each milling track 20a, 22a, 24a, includes a plurality of substantially parallel segments 20c, 22c, 24c, and a transverse, interconnecting segment 20d, 22d, 24d.

Guide 12 further includes legs 30, 32, 34, that extend from bottom surface 28 of guide 12, as shown in FIG. 1. More particularly, legs 30 extend from bottom surface 28 of anterior platform 20, legs 32 extend from bottom surface 28 of intermediate platform 22, and legs 34 extend from bottom surface 28 of distal platform 34. Each leg 30, 32, 34, includes a corresponding referencing end 30a, 32a, 34a. Each referencing end 30a, 32a, 34a, may have a partially rounded shape and/or smooth edges such that referencing ends 30a, 32a, 34a, can be rested against cartilage or soft tissue without puncturing the cartilage.

In addition to having milling tracks 20a, 22a, 24a, guide 12 may further include at least one cut referencing surface 38 for guiding cutting tool 16 (FIG. 7B) across distal end 102 of femur 100. As shown in FIGS. 5 and 6, cut referencing surface 38 of guide 12 is a planar surface defined by distal platform 24 and leg 34 of guide 12. In the illustrated embodiment, cut referencing surface 38 of guide 12 extends in a direction substantially perpendicular to distal platform 24 of guide 12. Although cut referencing surface 24 is illustrated as a single, planar surface, it is also within the scope of the present invention that guide 12 may include an elongate slot for guiding cutting tool 16 across distal end 102 of femur 100 in a captured manner.

Figure 7A:
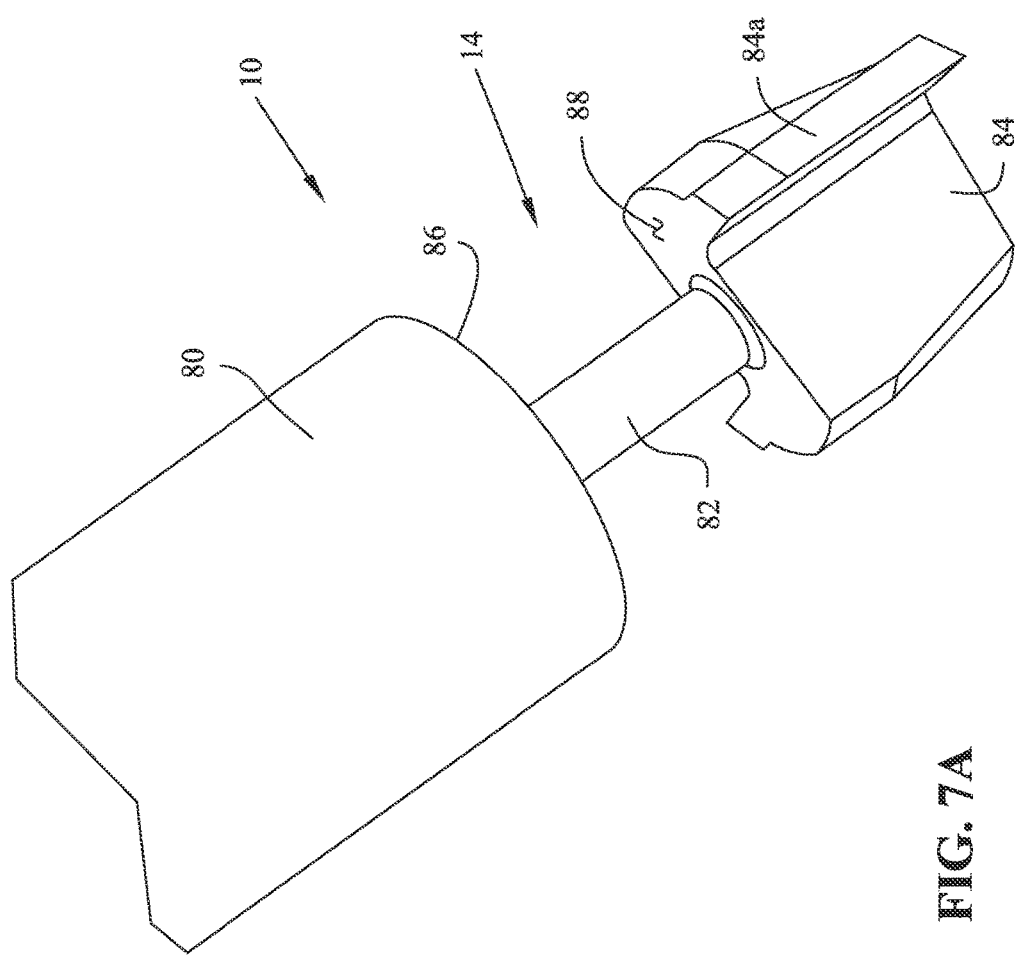
FIG. 7A is a perspective view of an exemplary milling tool of the present invention.
Figure 7B:
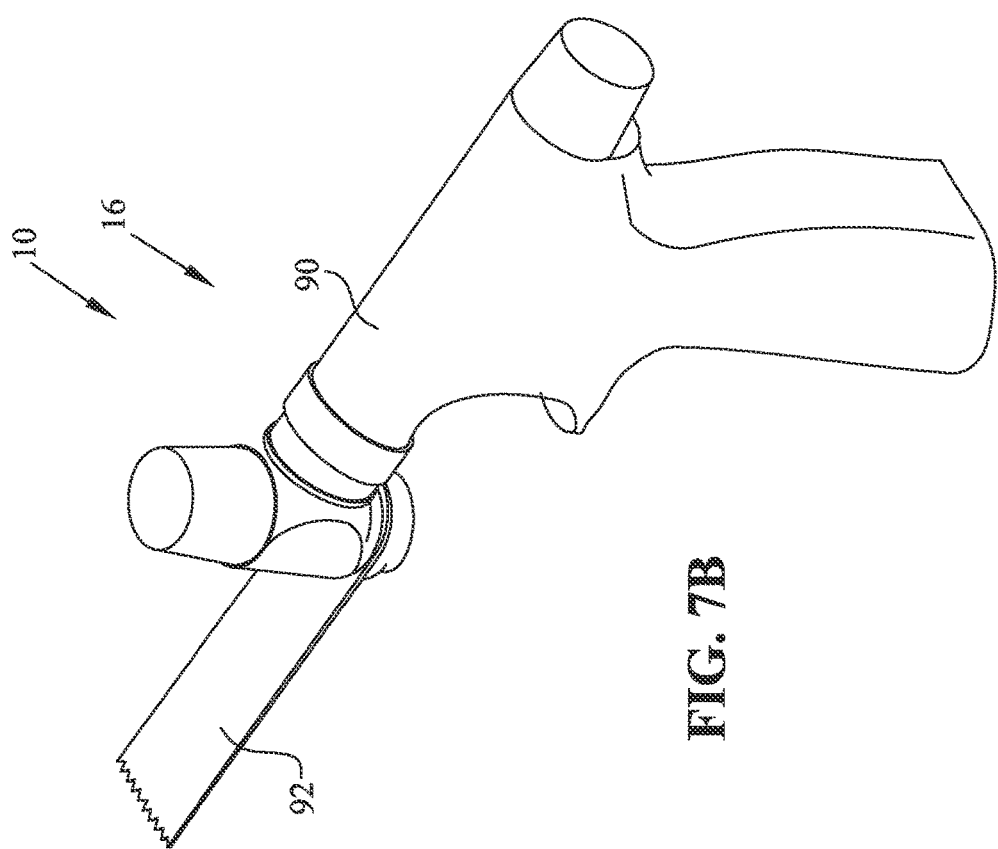
FIG. 7B is a perspective view of an exemplary cutting tool of the present invention.

Referring next to FIGS. 7A and 7B, exemplary surgical tools of orthopedic system 10 are illustrated. As shown in FIG. 7A, an exemplary milling tool 14 of orthopedic system 10 includes handpiece 80, rotating shaft 82 that extends through handpiece 80, and burr 84. Handpiece 80 of milling tool 14 includes top abutment surface 86 and burr 84 of milling tool 14 includes bottom abutment surface 88 that is spaced apart from top abutment surface 86 and faces top abutment surface 86. Burr 84 is coupled to rotating shaft 82 for rotation therewith. Burr 84 is configured to cut bone when it is placed against bone and rotated via rotating shaft 82. For example, burr 84 may include teeth 84a that are configured to cut bone. As shown in FIG. 7B, an exemplary cutting tool 16 of orthopedic system 10 includes handpiece 90 and an oscillating blade 92 that moves relative to handpiece 90 to cut bone.

Figure 8:
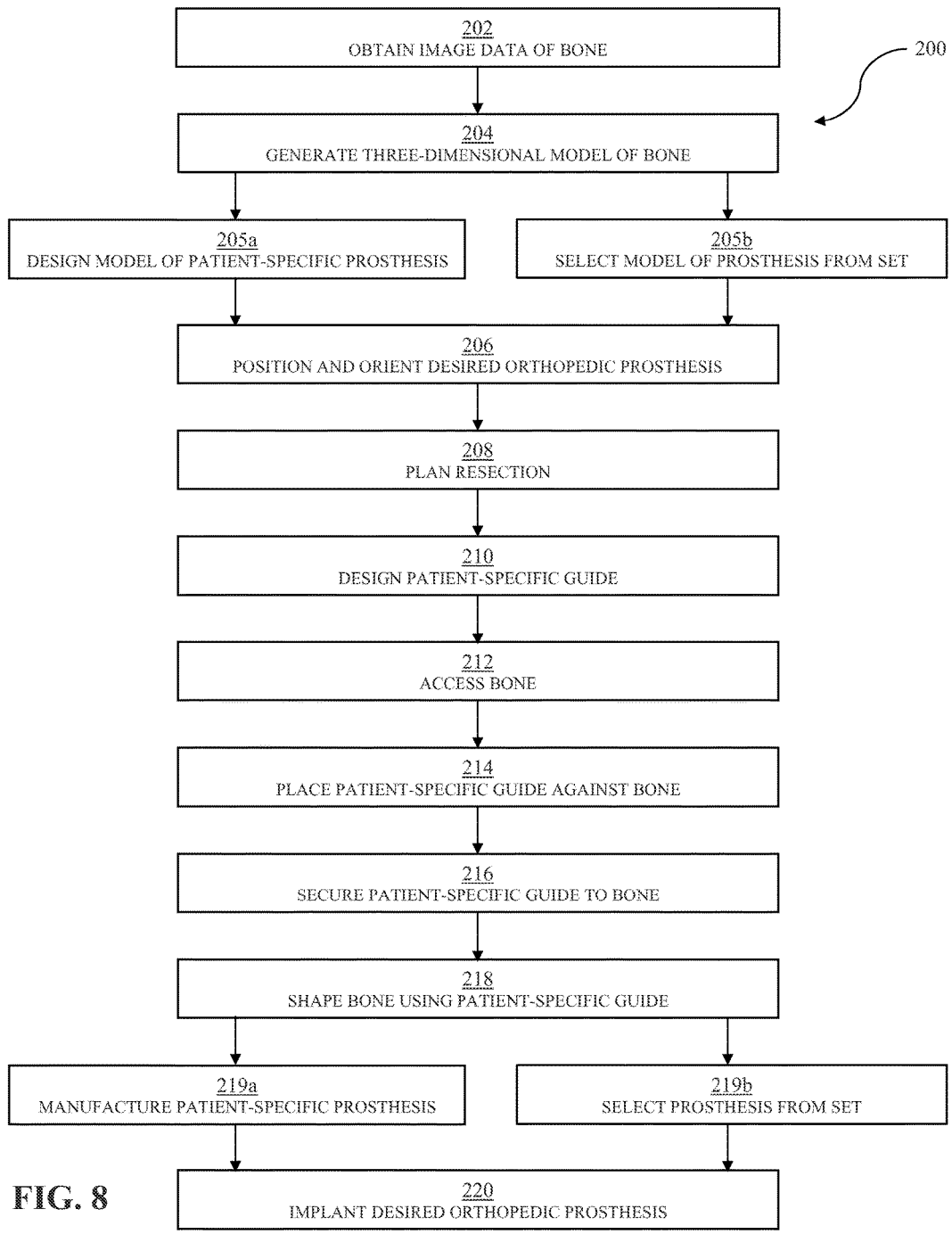
FIG. 8 is a flow chart of an exemplary method of the present invention.

Referring next to FIG. 8, an exemplary method 200 is provided for using a patient-specific guide 12 to prepare distal end 102 of femur 100.

First, in step 202 of method 200, the surgeon obtains image data of a patient's knee joint, including distal end 102 of femur 100, using a suitable imaging modality, such as magnetic resonance imaging (MRI), computed tomography (CT), ultrasound, or any another suitable imaging technique by which a volumetric, three dimensional image data set of the patient's joint may be obtained.

Optionally, the patient's knee joint may be placed in extension and tension while obtaining the imaging data. In patients who have arthritis or another disease or condition that affects the knee joint, for example, it may be helpful for the surgeon to assess the joint space between distal end 102 of femur 100 and the proximal end of the tibia (not shown) in tension to properly size the orthopedic prosthesis and to optimally reconstruct the knee joint. A suitable brace (not shown) may be applied about the knee joint or may be used to pull on the ankle, for example, in order to place the knee joint in tension when the patient's leg is extended. In this manner, when the imaging data is obtained, femur 100, the tibia (not shown), and the surrounding soft tissue are all visible about the joint space such that the surgeon may evaluate soft tissue laxity to properly determine the size and position of the orthopedic prosthesis, as discussed further below.

In addition to obtaining three dimensional imaging data of the knee joint when the knee is in extension, further imaging data may also be obtained of the knee joint in flexion, such as in mid flexion, in 90° flexion, or in full flexion. In one embodiment, additional three dimensional volumetric scans may be obtained in each of the foregoing positions. Alternatively, a two-dimensional imaging modality, such as an X-ray or fluoroscopy, may be used to obtain additional images in one or more positions in which the knee joint is in flexion, and a tension brace of the type described above may be used to assess laxity in the joint space. As described below, this additional imaging data may be used to construct a computer model of the knee joint and/or aid in the determination of the size and positioning of the orthopedic prosthesis.

Next, in step 204 of method 200, the imaging data of femur 100 obtained during step 202 may be processed by a computer planning system which includes suitable computer software to generate a three-dimensional computer model of femur 100. For example, the computer planning system may include image processing software that is able to segment, or differentiate, the desired anatomic structure (e.g., bone tissue) from undesired structures (e.g., the surrounding soft tissue in the joint). Then, the image processing software generates a computer model of the desired structure. One suitable method for generating a computer model of a desired anatomic structure involves assigning a grey value to each pixel of the imaging data, setting a threshold grey value, and segmenting desired pixels from undesired pixels based on the threshold grey value, as discussed in U.S. Pat. No. 5,768,134 to Swaelens et al., the disclosure of which is expressly incorporated herein by reference.

Using the computer model from step 204, the surgeon then selects a model of a desired prosthesis. According to an exemplary embodiment of the present invention, the computer planning system displays the computer model to the surgeon so that the surgeon can evaluate the anatomy of the joint to determine the implant solution that is optimized for the anatomical needs of the patient. Selecting the model of the desired prosthesis may involve designing a custom, patient-specific prosthesis in step 205a of method 200 or choosing a standard prosthesis from a set of known orthopedic prostheses in step 205b of method 200. For example, in step 205a, the surgeon or computer planning system may design a model of a patient-specific implant that best matches the anatomical needs of the patient. Alternatively, in step 205b, the surgeon or computer planning system may access a digital database or library of known orthopedic prostheses and select a model of a desired prosthesis from the database.

Then, in step 206 of method 200, the surgeon uses the computer model of femur 100 to position and orient the desired orthopedic prosthesis from step 205 relative to the bone. It is within the scope of the present invention that the orienting and positioning step 206 may occur after or simultaneously with the selecting step 205. According to an exemplary embodiment of the present invention, the surgeon overlays a digital representation or image of the desired prosthesis onto the computer model of the bone to ensure the proper size of the desired prosthesis and the proper orientation of the desired prosthesis relative to the bone.

In certain embodiments, the surgeon or computer planning system may evaluate soft tissue laxity to properly size multiple prostheses simultaneously. For example, the computer planning system may evaluate soft tissue laxity in the knee joint to simultaneously size a distal femoral prosthesis 50 (FIG. 10) and a proximal tibial prosthesis (not shown). Also, if multiple data sets of the knee joint in various positions of extension and flexion have been obtained, the same may be used for modeling a dynamic representation of the joint in which the surgeon may assess the joint in multiple positions of extension and flexion.

After the surgeon plans the size and location of the desired prosthesis using the computer model during step 206, the computer planning system determines at step 208 of method 200 which portions of the bone must be removed from the computer model to receive the desired prosthesis. In one embodiment, the computer planning system may identify for removal areas of overlap between the computer model of the bone and the digital model of the desired prosthesis. For example, using the computer model of the bone and the digital model of the desired prosthesis, the computer planning system may determine that a cavity must be formed in anterior surface 104 and distal surface 106 of femur 100, that posterior surface 108 of femur 100 must be cut along medial condyle 110 and/or lateral condyle 112, and that anchor holes must be drilled into femur 100 so that femur 100 may receive the desired distal femoral prostheses 50 (FIG. 10).

Next, in step 210 of method 200, the computer planning system designs a custom, patient-specific guide 12 based on the calculations from step 208. For example, the computer planning system may determine the shape and size of platforms 20, 22, 24, milling tracks 20a, 22a, 24a, and legs 30, 32, 34, of the patient-specific guide 12. The patient-specific guide 12 may be an entirely custom product that is manufactured using a casting/molding process or a rapid prototyping process, such as 3-D printing, stereolithography, selective laser sintering, fused deposition modeling, laminated object manufacturing, or electron beam melting, for example. Alternatively, the patient-specific guide 12 may be manufactured by removing material from a standard guide (e.g. from legs 30, 32, 34, of a standard guide).

Figure 14:
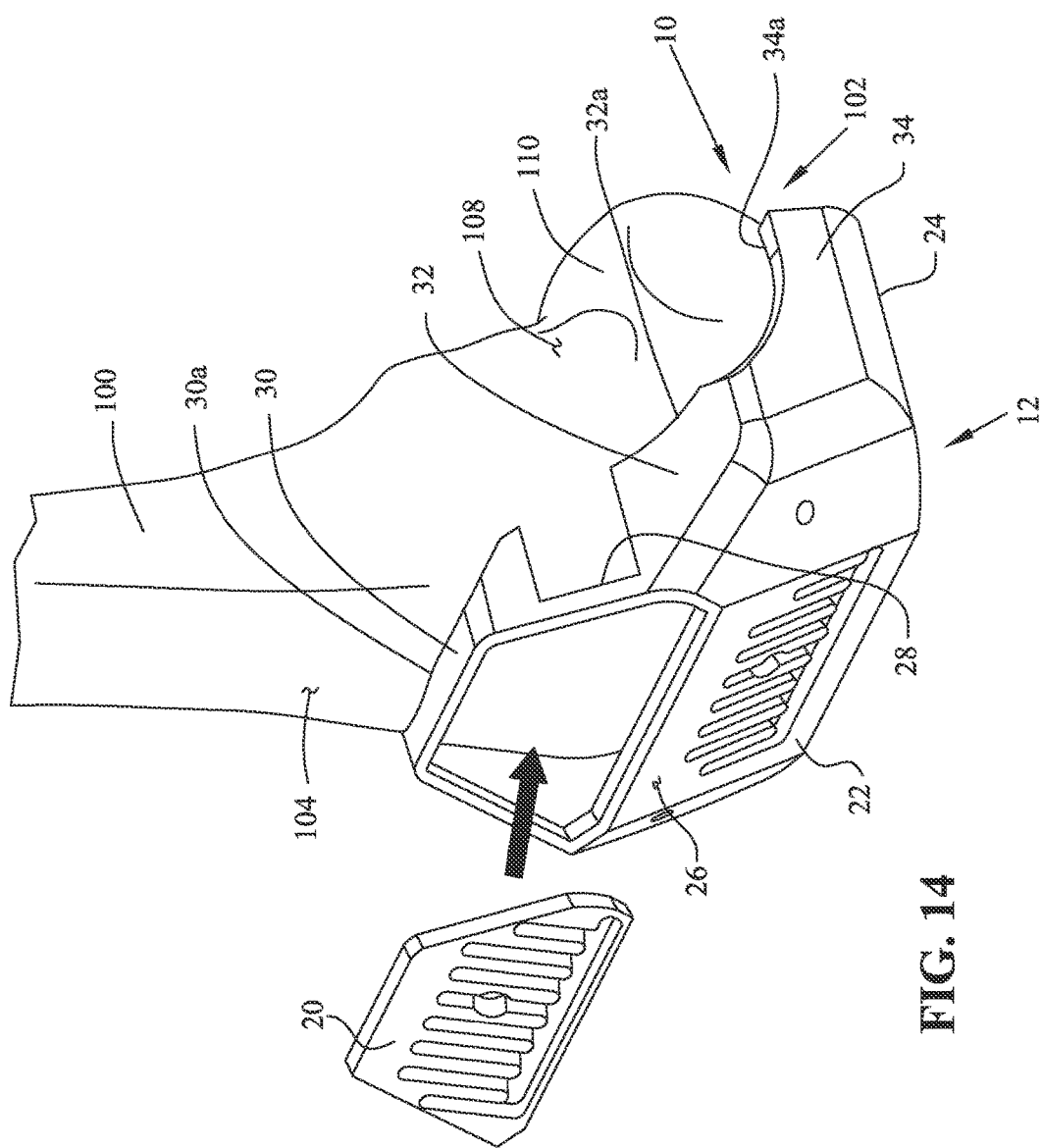
FIG. 14 is a medial perspective view of another exemplary patient-specific guide of the present invention, the patient-specific guide having a modular platform, which may be used for intraoperative customization.

Guide 12 may be constructed of a material that is able to withstand contact from milling tool 14 (FIG. 7A) and/or cutting tool 16 (FIG. 7B). In certain embodiments, guide 12 may be constructed entirely of a suitable plastic or metal. In other embodiments, guide 12 may be constructed of more than one material. For example, platforms 20, 22, 24, and milling tracks 20a, 22a, 24a, of guide 12 may be constructed of metal to withstand contact from milling tool 14 (FIG. 7A), while legs 30, 32, 34, of guide 12 may be constructed of plastic. In this example, the metallic platforms 20, 22, 24, may be standard, ready-made components that are snapped into the custom-made, plastic legs 30, 32, 34, as shown in FIG. 14. In another example, the majority of guide 12 may be constructed of plastic except for a metallic shield or plate 29 attached to bottom surface 28 of guide 12 to withstand contact from milling tool 14 (FIG. 7A), as shown in FIG. 15.

Figure 15:
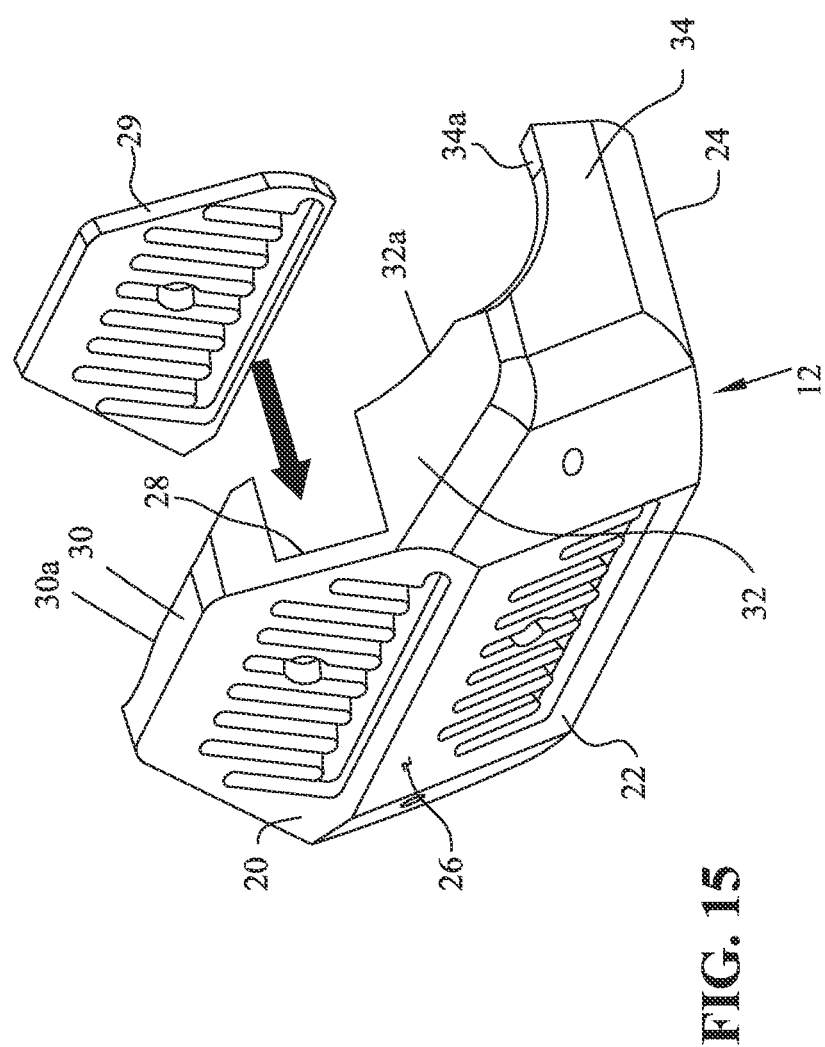
FIG. 15 is a medial perspective view of yet another exemplary patient-specific guide of the present invention, the patient-specific guide having a removable bottom plate, which may be used for intraoperative customization.

The modular guides 12 of FIGS. 14 and 15 may permit intraoperative customization. For example, a set of modular metallic platforms 20, 22, 24, may be provided, and the surgeon may choose, intraoperatively, desired platforms 20, 22, 24, from the set.

Then, in step 212 of method 200, the surgeon accesses distal end 102 of femur 100, such as using a minimally invasive surgical procedure, and, if necessary, the surgeon moves the patella (not shown) away from femur 100.

After distal end 102 of femur 100 is exposed in step 212, the surgeon continues to step 214 of method 200 and places the patient-specific guide 12 against femur 100. First, the surgeon orients the patient-specific guide 12 with bottom surface 28 of guide 12 facing toward femur 100 and top surface 26 of guide 12 facing away from femur 100, as shown in FIG. 1. The surgeon then places legs 30, 32, 34, of guide 12 against femur 100. Because legs 30, 32, 34, project beyond bottom surface 28 of guide 12, platforms 20, 22, 24, of guide 12 hover above femur 100 when legs 30, 32, 34, contact femur 100, as shown in FIG. 1.

According to an exemplary embodiment of the present invention, the patient-specific guide 12 conforms to femur 100 at a single predetermined location. For example, referencing ends 30a, 32a, 34a, of legs 30, 32, 34, may be shaped to match the contour of femur 100 at a single predetermined location. In the illustrated embodiment, referencing end 30a of leg 30 is shaped to match the contour of anterior surface 104 of femur 100 beneath anterior platform 20 of guide 12 (FIG. 2), referencing end 32a of leg 32 is shaped to match the contour of anterior surface 104 of femur 100 beneath intermediate platform 22 of guide 12 (FIG. 2), and referencing end 34a of leg 34 is shaped to match the contour of distal surface 106 of femur 100 beneath distal platform 24 of guide 12 (FIG. 6). In this exemplary embodiment, the surgeon is able to ensure that guide 12 is properly aligned by visualizing all of the legs 30, 32, 34, resting flush against femur 100 and/or by receiving tactile feedback of the fit between guide 12 and femur 100. If one leg 30, for example, is hovering away from femur 100, the surgeon will know to reposition guide 12 relative to femur 100 because the surgeon may visualize a gap between leg 30 and femur 100 and/or because the surgeon may feel that guide 12 is unbalanced on femur 100.

Once guide 12 is properly aligned with femur 100, the surgeon may temporarily secure guide 12 to femur 100 in step 216 of method 200. As shown in FIG. 3, the surgeon may temporarily secure guide 12 to femur 100 by inserting screws, nails, or other suitable anchors (not shown) through apertures 36 in guide 12 and into the bone of femur 100. Any suitable number and arrangement of apertures 36 may be provided in guide 12. For example, although apertures 36 are shown as being located in intermediate platform 22 of guide 12, apertures 36 may be located in anterior platform 20 and/or distal platform 24 of guide 12.

Figure 9:
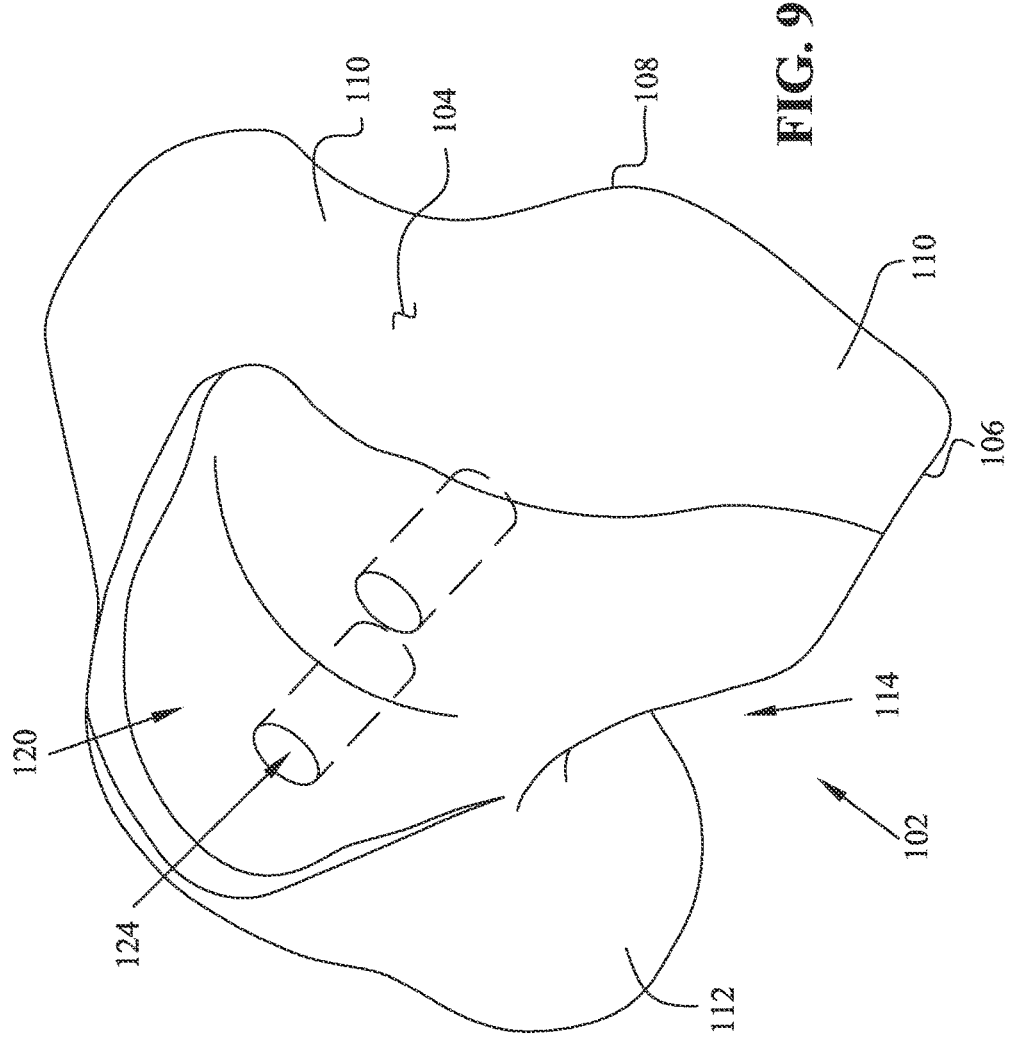
FIG. 9 is a medial perspective view of a prepared distal femur.

Next, in step 218 of method 200, the surgeon uses the patient-specific guide 12 to shape distal end 102 of femur 100. In operation, guide 12 (FIGS. 1-6) controls the position of milling tool 14 (FIG. 7A) relative to femur 100 so that milling tool 14 removes a desired portion of bone from femur 100. With guide 12 secured to femur 100, as shown in FIG. 1, the surgeon first inserts milling tool 14 into opening 20b, 22b, 24b, of a desired milling track 20a, 22a, 24a. Then, milling tool 14 is moved into the desired milling track 20a, 22a, 24a, with top abutment surface 86 of milling tool 14 abutting top surface 26 of guide 12 to prevent milling tool 14 from being pushed too far beneath guide 12 toward femur 100. Thus, the depth of insertion of burr 84 into femur 100 is governed by the distance between top surface 26 of guide 12 and femur 100, which distance may be varied by altering the length of legs 30, 32, 34, for example. Also, bottom abutment surface 88 of milling tool 14 may abut bottom surface 28 of guide 12 to prevent milling tool 14 from being pulled away from guide 12 and femur 100. As the surgeon moves milling tool 14 through milling tracks 20a, 22a, 24a, burr 84 rotates beneath platforms 20, 22, 24, of guide 12 to remove a desired portion of bone from femur 100. For example, as shown in FIG. 9, guide 12 and milling tool 14 may be used to mill cavity 120 into femur 100 that spans anterior surface 104 and distal surface 106 of femur 100.

It is within the scope of the present invention that platforms 20, 22, 24, of guide 12 may be non-planar, such that the depth of insertion of burr 84 into femur 100 varies across the surface of femur 100. An exemplary guide 12 and an exemplary milling tool 14 are described in U.S. patent application Ser. No. 11/687,161, entitled "SINGLE PLANE ANATOMIC REFERENCING TISSUE PREPARATION," the entire disclosure of which is expressly incorporated herein by reference.

Figure 12:
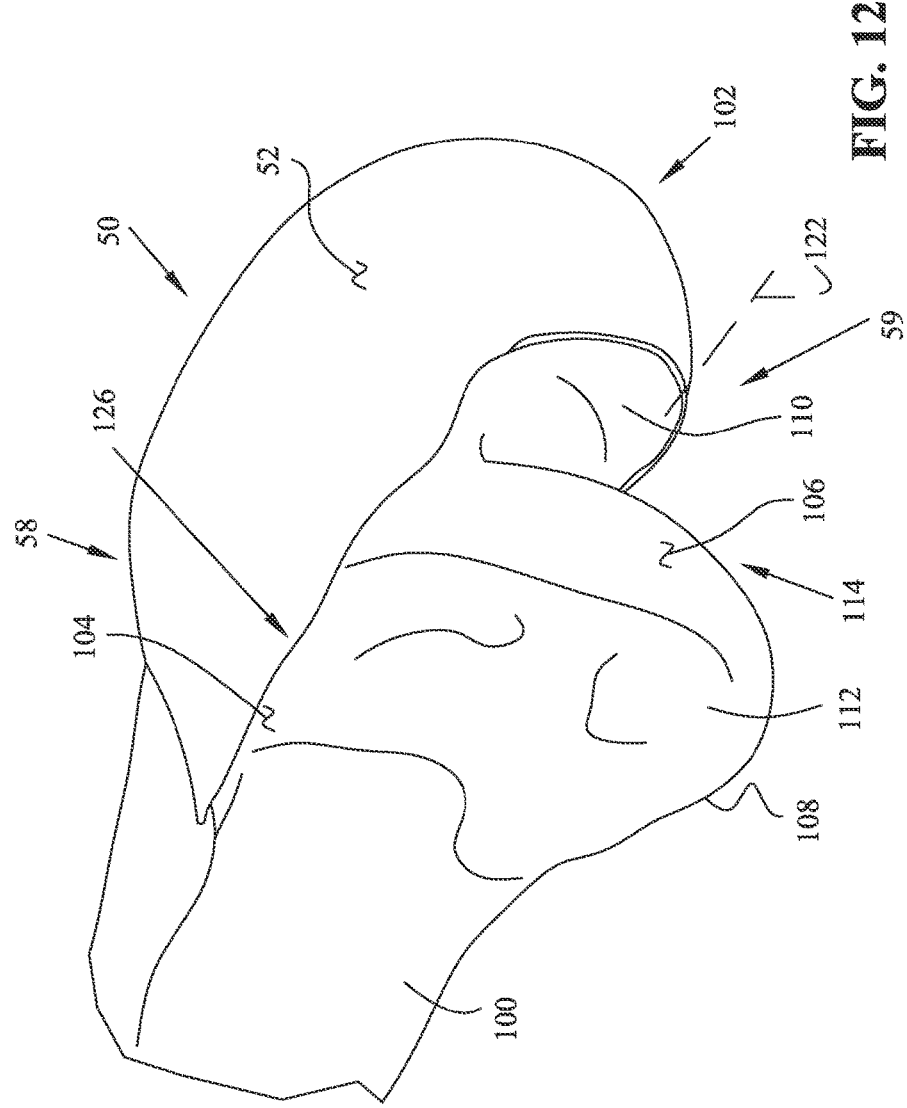
FIG. 12 is a lateral perspective view of the distal femoral prosthesis of FIG. 10 implanted onto the prepared distal femur.
Figure 13:
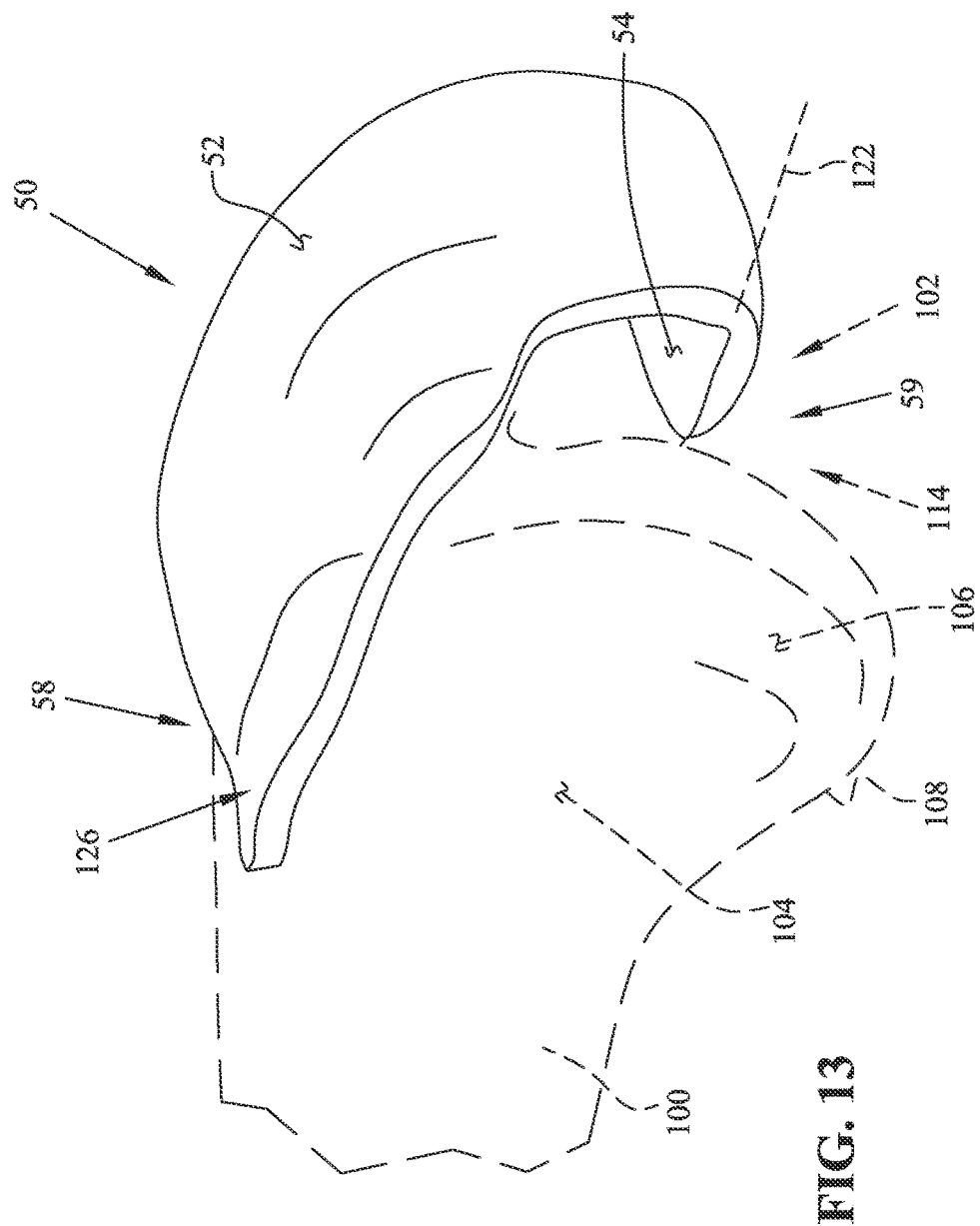
FIG. 13 is a view similar to FIG. 12 with the prepared distal femur shown in phantom.

In addition to milling femur 100 using guide 12 and milling tool 14, the surgeon may use guide 12 and cutting tool 16 (FIG. 7B) to cut portions of femur 100. For example, the surgeon may drag the oscillating blade 92 of cutting tool 16 along referencing surface 38 of guide 12 and posterior surface 108 of femur 100 (FIGS. 5 and 6) to resect medial condyle 110 and/or lateral condyle 112 along cut line 122 (FIGS. 12 and 13). It is also within the scope of the present invention that guide 12 may be provided with other cut referencing surfaces or cut slots so that the surgeon is able to cut other surfaces of femur 100, including anterior surface 104 and/or distal surface 106 of femur 100.

Guide 12 may include other features for preparing femur 100 to receive distal femoral prostheses 50 (FIG. 10). For example, it is within the scope of the present invention that guide 12 may include holes (not shown) for drilling anchor holes 124 (FIG. 9) into femur 100. These holes in guide 12 may be similar to apertures 36 in guide 12, which are described above for attaching guide 12 to femur 100.

According to an exemplary embodiment of the present invention, the bone actually removed from femur 100 using the patient-specific guide 12 during step 218 corresponds to the resection planned using the computer model of femur 100 during step 208. As discussed above in the description of step 208, the computer planning system may determine, for example, that a cavity must be formed in anterior surface 104 and distal surface 106 of femur 100, that medial condyle 110 and/or lateral condyle 112 must be cut along posterior surface 108 of femur 100, and that anchor holes must be drilled into femur 100. Then, in step 210, the computer planning system designs a patient-specific guide 12 that will guide resection of femur 100 as planned. For example, the computer planning system may vary the size and shape of platforms 20, 22, 24, milling tracks 20a, 22a, 24a, and legs 30, 32, 34, to design a patient-specific guide 12 that will guide resection of femur 100 as planned. Returning to the previous example, the surgeon may then use the patient-specific guide 12 to: (1) form cavity 120 in anterior surface 104 and distal surface 106 of femur 100 (FIG. 9) that corresponds to the planned cavity, (2) cut medial condyle 110 and/or lateral condyle 112 of femur 100 along cut line 122 (FIG. 12) that corresponds to the planned cut line, and/or (3) form anchor holes 124 in femur 100 (FIG. 9) that correspond to the planned anchor holes.

After preparing femur 100 in step 218, the desired distal femoral prosthesis 50 is provided to the surgeon. Providing the desired prosthesis may involve manufacturing a custom, patient-specific prosthesis in step 219a of method 200 based on the patient-specific prosthesis designed during step 205a. Alternatively, providing the desired prosthesis may involve choosing a standard prosthesis from a set of known orthopedic prostheses in step 219b of method 200 based on the model selected during step 205b.

According to an exemplary embodiment of the present invention, a patient-specific distal femoral prosthesis 50 may be provided in step 219a that is sized and shaped to replicate the portion of bone that was removed from femur 100 using guide 12. However, if the natural articulating surface of femur 100 had been damaged or had deteriorated, the patient-specific distal femoral prosthesis 50 may be sized and shaped to replicate the portion of bone that was removed from femur 100 using guide 12, as well as the portion of bone that was missing from femur 100 due to disease or traumatic injury, for example. In this embodiment, articulating surface 52 of distal femoral prosthesis 50 may be sized and shaped to replicate the natural articulating surface of femur 100.

Figure 11:
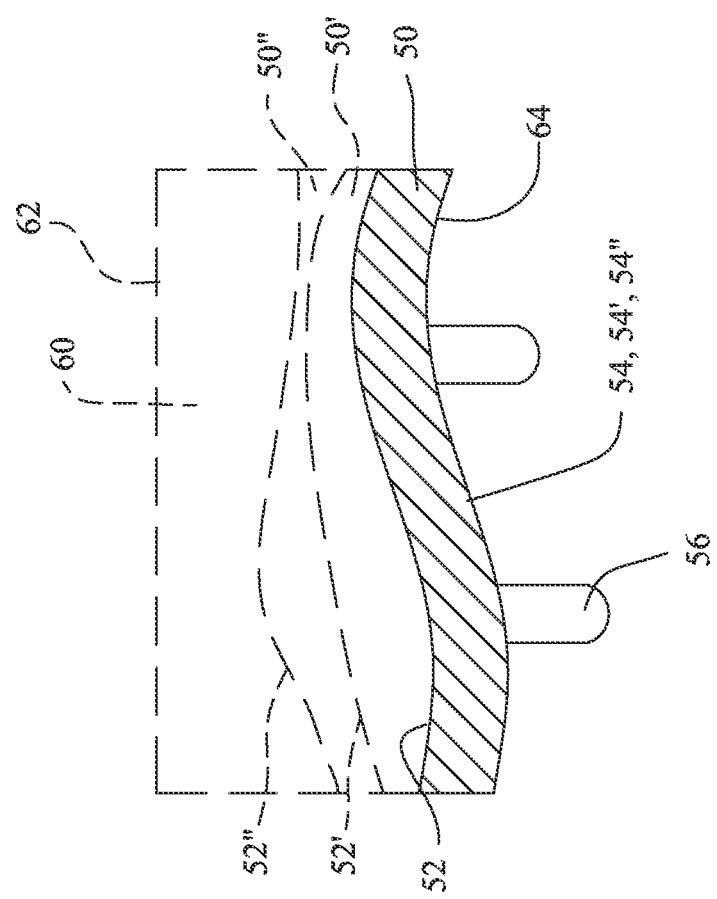
FIG. 11 is a cross-sectional view of the distal femoral prosthesis of FIG. 10, also showing in phantom a standard component from which the distal femoral prosthesis is formed.

According to another exemplary embodiment of the present invention, the same computer planning system that plans the desired resection may be used to design and/or manufacture a patient-specific distal femoral prosthesis 50. In certain embodiments, the patient-specific distal femoral prosthesis 50 may be an entirely custom product that is manufactured using a casting/molding process or a rapid prototyping process, such as 3-D printing, stereolithography, selective laser sintering, fused deposition modeling, laminated object manufacturing, or electron beam melting, for example. In other embodiments, and as shown in FIG. 11, the patient-specific distal femoral prosthesis 50 be manufactured by providing a bulk construct or block 60 having top surface 62 and a standard bottom surface 64 and then machining top surface 62 of block 60 to form the patient-specific distal femoral prosthesis 50, 50', 50'', having articulating surface 52, 52', 52'', that match each patient's particular anatomy and the same bone-engaging surfaces 54, 54', 54''. Advantageously, providing block 60 having a standard bottom surface 64 will standardize some features of the patient-specific guide 12.

Finally, in step 220 of method 200, the surgeon implants the desired distal femoral prosthesis 50 in distal end 102 of femur 100. Distal femoral prosthesis 50 may be a unicompartmental implant, a bicompartmental implant, or a total femoral implant, for example. An exemplary distal femoral prosthesis 50 is illustrated in FIG. 10 and includes a top articulating surface 52 and a bottom bone-engaging surface 54. Distal femoral prosthesis 50 may also include one or more anchors or pegs 56 that project from bone-engaging surface 54 of distal femoral prosthesis 50, as shown in FIG. 10.

In operation, the surgeon secures distal femoral prosthesis 50 to femur 100 with bone-engaging surface 54 of distal femoral prosthesis 50 abutting the prepared distal end 102 of femur 100, as shown in FIGS. 12 and 13. Distal femoral prosthesis 50 may be secured to femur 100 using a suitable adhesive such as bone cement or mechanical fasteners, for example. The attachment between distal femoral prosthesis 50 and femur 100 may be enhanced by inserting pegs 56 of distal femoral prosthesis 50 into anchor holes 124 of femur 100.

According to an exemplary embodiment of the present invention, distal femoral prosthesis 50 may be at least partially inlayed into the prepared distal end 102 of femur 100. For example, as shown in FIGS. 12 and 13, proximal end 58 of distal femoral prosthesis 50 fits within cavity 120 and is inlayed in femur 100. An inlayed prosthesis provides a smooth transition between the prosthesis and surrounding cartilage and/or bone, which may facilitate a smooth articulation with adjacent anatomical structures. In the illustrated embodiment, distal femoral prosthesis 50 is inlayed to provide a smooth transition region 126 between prosthesis 50 and anterior surface 104 of femur 100. For example, articulating surface 52 of distal femoral prosthesis 50 and anterior surface 104 of femur 100 may rest in substantially the same plane, such that articulation across surfaces 52, 104, is substantially continuous. Other portions of distal femoral prosthesis 50 may rest atop a prepared surface of femur 100. For example, as shown in 12, distal end 59 of distal femoral prosthesis 50 rests atop femur 100 along cut line 122.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopedic guide for preparing a particular patient's bone to receive a prosthesis using a milling tool with a rotating burr, the orthopedic guide comprising:
    a cutting platform having a top surface and a bottom surface adapted to face the patient's bone, the platform having an elongated milling track that extends through the platform from the top surface to the bottom surface of the platform, the milling track including a plurality of substantially parallel segments and a transverse interconnecting segment that joins together the plurality of substantially parallel segments, the milling track occupying an extent of the platform to guide the milling tool across the patient's bone with the burr of the milling tool rotating beneath the bottom surface of the platform to remove a first bone portion from the patient's bone; and
    a plurality of legs projecting from the bottom surface of the platform, the legs being adjacent to an outer periphery of the platform, each of the plurality of legs comprising a referencing end that is contour-matching fabricated as a function of a three-dimensional computer model of the patient's bone to be adapted to abut the patient's bone such that the bottom surface of the platform is adapted to be spaced from the patient's bone when the referencing ends of the plurality of legs abut the patient's bone, the bottom surface being spaced from a native surface of the patient's bone over the extent of the platform occupied by the milling track, the referencing ends of the plurality of legs adapted to cooperate to locate the orthopedic guide at a single predetermined location of the patient's bone, the plurality of legs distributing a majority of force of the milling tool applied against the platform to the bone.

2. The orthopedic guide of claim 1, wherein the platform includes an anterior portion, an intermediate portion that extends obtusely from the anterior portion of the platform, and a distal portion that extends obtusely from the intermediate portion of the platform, the orthopedic guide configured to be adapted for use with the patient's femur such that the anterior portion of the platform is adapted to rest above an anterior surface of the patient's femur and the distal portion of the platform is adapted to rest above a distal surface of the patient's femur.

3. The orthopedic guide of claim 1, wherein the platform includes an anterior portion and a distal portion that extends transverse to the anterior portion of the platform, the orthopedic guide configured to be adapted for use with the patient's femur such that the anterior portion of the platform is adapted to rest above an anterior surface of the patient's femur and the distal portion of the platform is adapted to rest above a distal surface of the patient's femur.

4. The orthopedic guide of claim 1, wherein the milling track includes an enlarged opening for receiving the burr of the milling tool, the milling track narrowing in width apart from the enlarged opening to retain the burr of the milling tool beneath the platform.

5. The orthopedic guide of claim 1, wherein the platform further defines a planar cut referencing surface that is configured to be adapted to guide a cutting tool across the patient's bone to be adapted to remove a second bone portion from the patient's bone.

6. Use of the orthopedic guide of claim 1, wherein the plurality of legs contact the bone to distribute the majority of the force of the milling tool applied against the platform to the bone.

7. The use of the orthopedic guide according to claim 6, wherein the orthopedic guide is used without fasteners to distribute the majority of the force of the milling tool applied against the platform to the bone.

8. An orthopedic guide for preparing a particular patient's bone to receive a prosthesis using a milling tool with a rotating burr, the orthopedic guide comprising:

a cutting platform having a top surface and a bottom surface adapted to face the patient's bone, the platform having an elongated milling track that extends through the platform from the top surface to the bottom surface of the platform, the milling track including a plurality of substantially parallel segments and a transverse interconnecting segment that joins together the plurality of substantially parallel segments, the milling track occupying an extent of the platform inward of an outer periphery of the platform to guide the milling tool across the patient's bone with the burr of the milling tool rotating beneath the bottom surface of the platform to remove a first bone portion from the patient's bone; and a plurality of legs projecting from the bottom surface of the platform, the legs being adjacent to the outer periphery of the platform, each of the plurality of legs comprising a referencing end that is contour-matching fabricated as a function of a three-dimensional computer model of the patient's bone to be adapted to abut the patient's bone such that the bottom surface of the platform is adapted to be spaced from the patient's bone when the referencing ends of the plurality of legs abut the patient's bone, the bottom surface being spaced from a native surface of the patient's bone over the extent of the platform occupied by the milling track and over a portion of the platform between the outer periphery and the extent thereof, the referencing ends of the plurality of legs adapted to cooperate to locate the orthopedic guide at a single predetermined location of the patient's bone, the plurality of legs distributing a majority of force of the milling tool applied against the platform to the bone.

9. The orthopedic guide of claim 8, wherein the plurality of legs are spaced apart about the outer periphery of the platform.

10. The orthopedic guide of claim 8, wherein the platform includes an anterior portion, an intermediate portion that extends obtusely from the anterior portion of the platform, and a distal portion that extends obtusely from the intermediate portion of the platform, the orthopedic guide configured to be adapted for use with the patient's femur such that the anterior portion of the platform is adapted to rest above an anterior surface of the patient's femur and the distal portion of the platform is adapted to rest above a distal surface of the patient's femur.

11. The orthopedic guide of claim 10, wherein the milling track comprises an anterior track portion, an intermediate track portion, and a distal track portion, each respectively spanning the anterior portion, the intermediate portion, and the distal portion of the platform.

12. The orthopedic guide of claim 8, wherein the platform includes an anterior portion and a distal portion that extends transverse to the anterior portion of the platform, the orthopedic guide configured to be adapted for use with the patient's femur such that the anterior portion of the platform is adapted to rest above an anterior surface of the patient's femur and the distal portion of the platform is adapted to rest above a distal surface of the patient's femur.

13. The orthopedic guide of claim 8, wherein the milling track includes an enlarged opening for receiving the burr of the milling tool, the milling track narrowing in width apart from the enlarged opening to retain the burr of the milling tool beneath the platform.

14. The orthopedic guide of claim 8, wherein the platform further defines a planar cut referencing surface that is configured to be adapted to guide a cutting tool across the patient's bone to be adapted to remove a second bone portion from the patient's bone.

15. The orthopedic guide of claim 14, wherein the cut referencing surface is located on an exterior surface of the platform.

16. The orthopedic guide of claim 8, wherein the plurality of legs are integrally fixed to the platform.

17. The orthopedic guide of claim 8, wherein at least one of the legs extends from end to end of an edge of the platform.

18. The orthopedic guide of claim 8, wherein the platform has at least three edges and defines a plane, one of the plurality of legs projecting from the bottom surface at three of the edges of the platform, said plane being parallel to the bottom surface of the platform.

19. Use of the orthopedic guide of claim 8, wherein the plurality of legs contact the bone to distribute the majority of the force of the milling tool applied against the platform to the bone.

20. The use of the orthopedic guide according to claim 19, wherein the orthopedic guide is used without fasteners to distribute the majority of the force of the milling tool applied against the platform to the bone.

* * * * *